United States Patent [19]
Cisko, Jr. et al.

[11] Patent Number: 5,865,819
[45] Date of Patent: Feb. 2, 1999

[54] TWO-POUCH OSTOMY APPLIANCE WITH SEPARATE INNER AND OUTER ADHESIVE FLANGES

[75] Inventors: George J. Cisko, Jr., Spring Grove; George M. Nowak, Lake Villa, both of Ill.

[73] Assignee: Hollister Incorporated, Libertyville, Ill.

[21] Appl. No.: 883,674

[22] Filed: Jun. 27, 1997

[51] Int. Cl.$^6$ ........................................ A61F 5/44
[52] U.S. Cl. ........................ 604/339; 604/327; 604/338; 604/355
[58] Field of Search .................... 604/277, 327, 604/332–345, 355

[56] References Cited

U.S. PATENT DOCUMENTS

| | | |
|---|---|---|
| 3,089,493 | 5/1963 | Galindo . |
| 4,816,027 | 3/1989 | Gilchrist et al. ........................ 604/339 |
| 4,826,496 | 5/1989 | Petersen . |
| 5,591,144 | 1/1997 | Smith et al. ........................... 604/327 |
| 5,769,831 | 6/1998 | Freeman et al. ........................ 604/332 |
| 5,785,695 | 7/1998 | Sato et al. ................................ 604/339 |

FOREIGN PATENT DOCUMENTS

| | | |
|---|---|---|
| 2273052 | 6/1994 | United Kingdom . |
| 2290712 | 1/1996 | United Kingdom . |

*Primary Examiner*—John G. Weiss
*Assistant Examiner*—Dennis Ruhl
*Attorney, Agent, or Firm*—Tilton Fallon Lungmus

[57] ABSTRACT

An ostomy appliance comprises two pouches, one being located within and extractable from the other. The inner pouch has a stoma-receiving orifice in its bodyside wall and an annular adhesive flange externally secured to that bodyside wall about the orifice. The outer pouch has a substantially larger opening in its bodyside wall and a second annular adhesive flange is secured to that wall and surrounds the first adhesive flange of the inner pouch. The two flanges are spaced from each other and the only connection between the two pouches occurs along their uppermost margins. The inner pouch is provided with a tear line along its upper margin, and the outer pouch has an access flap in its obverse wall which may be torn downwardly for gaining access to and removing the inner pouch from the outer pouch.

20 Claims, 2 Drawing Sheets

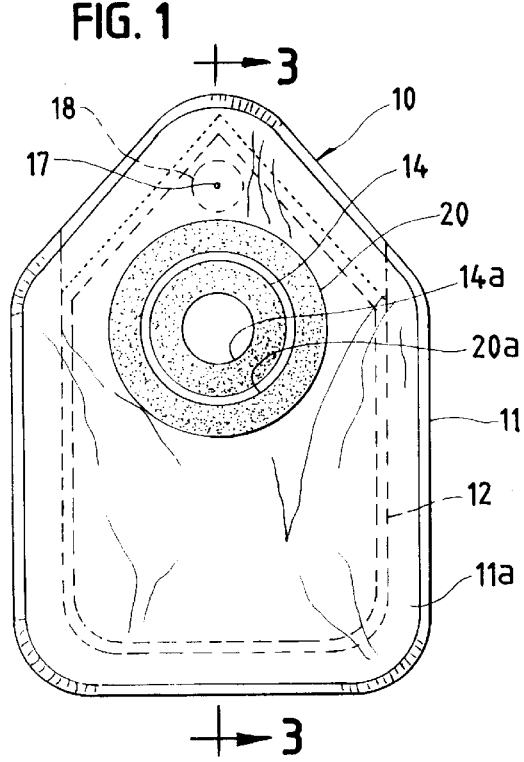
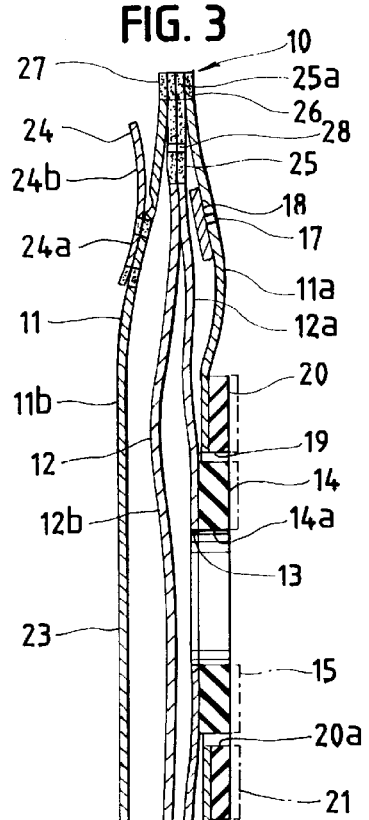
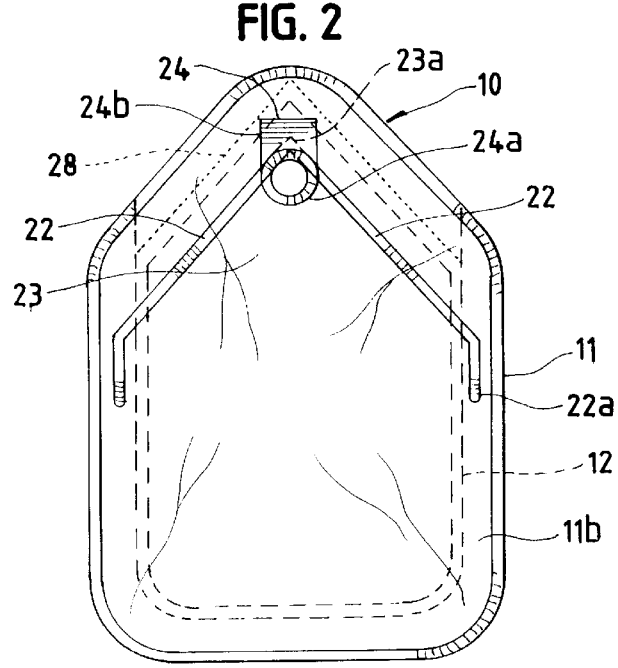

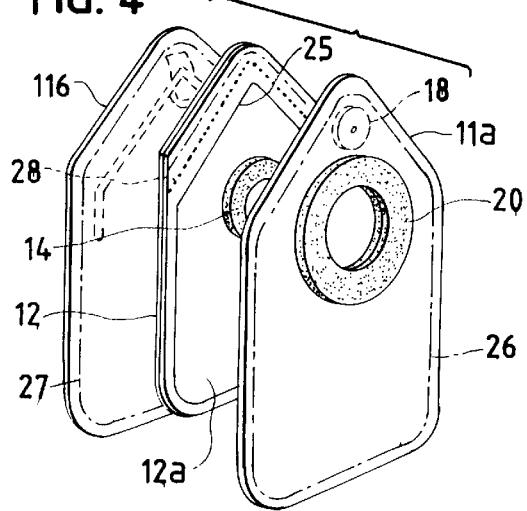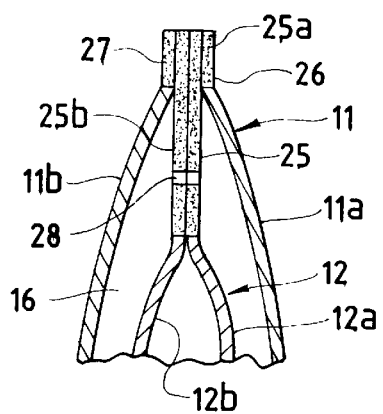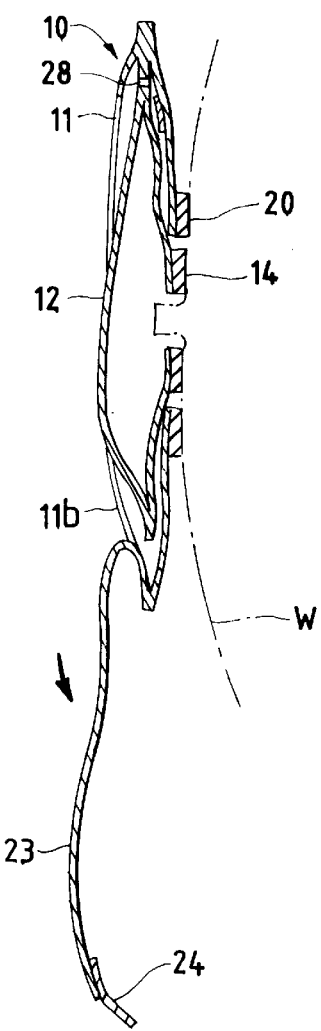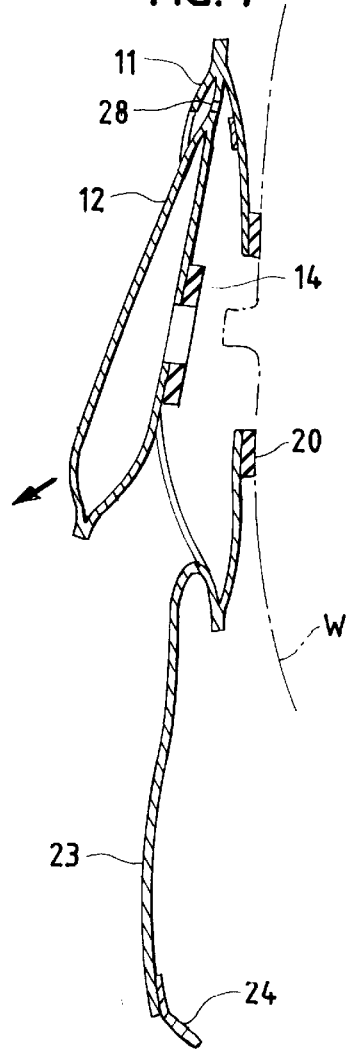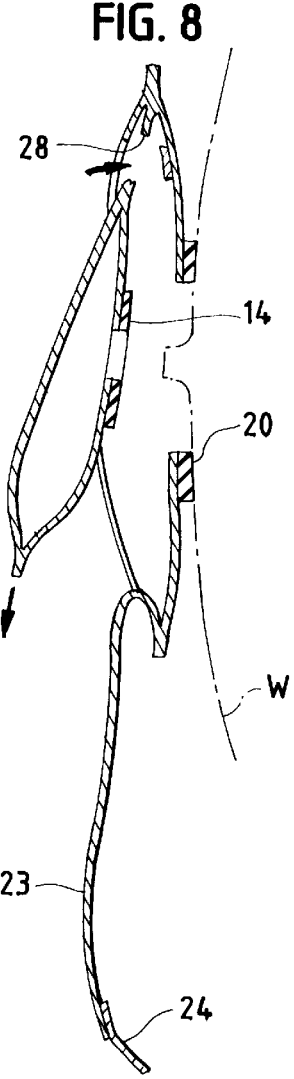

TWO-POUCH OSTOMY APPLIANCE WITH SEPARATE INNER AND OUTER ADHESIVE FLANGES

BACKGROUND AND SUMMARY

Two-pouch ostomy appliances are disclosed, for example, in U.S. Pat. Nos. 3,089,493 and 4,826,495 and in published British applications GB 2,273,052A and 2,290,712A. A main purpose for such a two-piece system is to provide an inner pouch that is toilet-disposable, that is, one which may be discarded into the water of a toilet bowl and is capable of being flushed away without obstructing or damaging the sewer lines. Such a pouch should be degradable and, as disclosed in the art, may even be made dissolvable or disintegratable in the turbulent water of a flush toilet.

The outer pouch may be reusable and need not be toilet-disposable. Since it does not directly receive waste material (but only surrounds the inner pouch which in turn collects such material), the outer pouch, if it is not reused, may be conveniently discarded in any suitable waste receptacle.

The materials from which inner pouches had been formed in the past may or may not be gas permeable, but such materials are generally regarded as poor odor barriers. In any event, to prevent such an inner pouch from inflating in use because of flatus gasses, even an inner pouch formed of gas-impermiable material should be provided with venting means. To avoid compromising the flushability of the inner pouch, such venting means should not include a deodorizing gas filter even in those constructions in which an inner pouch is formed of an inner pouch having odor barrier properties. On the other hand, the non-flushable outer pouches of a two-pouch appliance would normally be formed of a material having odor barrier properties and also having a gas filter capable of deodorizing gasses escaping from the appliance.

Such a two-pouch system generally requires that the pouches be connected in use but separable from each other when the inner pouch is to be discarded into a flush toilet. In British application GB 2,273,052A, the two pouches are joined to the same annular adhesive flange that secures the appliance to the peristomal skin surfaces of a patient and, hence, the pouches are secured together in the region of the stoma-receiving orifice of the flange. Means are disclosed for making the attachment between the flange and the outer pouch a disruptable one. The published British application describes and shows (FIG. 6) that the outer pouch may be detached from the flange and drawn away from the inner pouch while the latter remains adhesively secured to the patient.

As a practical matter, efforts to remove an outer pouch while an inner pouch remains in place might be a difficult and possibly messy procedure. The force required to disconnect an outer pouch from the flange might also result in detaching the flange from the patient, preventing separation of the two pouches in the manner described in the patent and possibly resulting in leakage and loss of control over both pouches. Perhaps for those reasons, the patentee instructs users to follow a different procedure in the marketing of its commercial product. Specifically, the instructional literature accompanying the commercial product disclosed in this published application directs users to remove both pouches at the same time by peeling the adhesive flange (wafer) away from the skin and only then, after both pouches are removed, to proceed with separation of the pouches. Even then, such separation may be difficult and messy since a user is instructed to break the attachment between the adhesive flange and the outer pouch by gripping the outer pouch and exerting a sharp outward movement to free the outer pouch from the flange. If successfully done, that leaves the outer pouch with a torn opening that approximates the size of the flange (to which it is no longer connected) and the user must then extract the inner pouch and its contents through the torn opening in the outer pouch.

A main aspect of this invention is to provide a two-pouch system that is more user-friendly and does not require a user to disconnect the inner and outer pouches from each other in the region of a stoma-receiving orifice as a prerequisite to separation of the pouches from each other. In a removal operation utilizing the system of this invention, a user simply tears open an enlarged flap on the obverse or front wall of the outer pouch (preferably while both pouches are still being worn), peels an adhesive attachment flange exclusively for the inner pouch away from the skin, and then grips the inner pouch and tears it free along a tear line extending along its upper margin (or its upper side margins), drawing the inner pouch out of the outer pouch through the enlarged flap opening formed in the latter. After discharging the inner pouch and its contents into a flush toilet, a user then removes the outer pouch from its adhesive attachment to the skin.

An important feature permitting such user-friendly operation is the fact that the two pouches are not connected to each other about the stoma-receiving orifice. In contrast to the prior art systems, each pouch has its own annular adhesive attachment flange or wafer, and the two flanges are not connected in use. The inner pouch has a first flange externally secured thereto about the orifice in its bodyside wall, and the outer pouch has a second adhesive flange secured to its bodyside wall and extending about, and spaced from, the first adhesive flange of the inner pouch. Therefore, the smaller annular flange of the inner pouch may be easily peeled away from the skin without resistance from the larger flange of the outer pouch which most advantageously remains attached to the skin for later removal.

Briefly, the ostomy appliance of this invention includes an inner pouch having a bodyside wall with a stoma-receiving orifice in that wall. An outer pouch surrounds the inner pouch and also has a bodyside wall with an opening that is generally concentric with and substantially larger than the orifice of the inner pouch. The inner pouch has a upper marginal portion that is disposed between and sealed (thermally or adhesively) to the upper edge portions of the bodyside wall and obverse wall of the outer pouch, with the upper marginal portion of the inner pouch having a sealed lower section that is located below the seal between the marginal portion and the walls of the outer pouch. A tear line extends across the the upper marginal portion of the inner pouch and, since the upper marginal portion is the only connection between the two pouches, separation along that tear line disconnects the pouches from each other.

Means are provided by the obverse wall of the outer pouch for accessing and extracting the inner pouch. In a preferred embodiment, such means takes the form of a flap portion at least partially defined by downwardly and outwardly diverging lines of weakness formed in the obverse wall of the pouch. The flap portion may be generally triangular in shape, and gripping means may be provided at the upper apex of the triangle to facilitate execution of the downward and outward tearing operation when access and removal of the inner pouch are desired.

Other features, advantages and objects of the invention will become apparent from the specification and drawings.

DRAWINGS

FIG. 1 is an elevational view of an appliance embodying the invention, such appliance being viewed from the bodyside surface thereof.

FIG. 2 is an elevational view from the obverse surface of the appliance.

FIG. 3 is an enlarged and somewhat schematic sectional view taken along line 3—3 of FIG. 1.

FIG. 4 is an exploded perspective view depicting the inner pouch and its relation to the separated walls of the outer pouch.

FIG. 5 is a greatly enlarged fragmentary sectional view of the upper marginal portion of the appliance.

FIG. 6 is a sectional view schematically illustrating a first step in the removal procedure.

FIG. 7 is a sectional view similar to FIG. 6 but illustrating a second step in the removal procedure.

FIG. 8 is a sectional view illustrating a further step in such procedure.

DETAILED DESCRIPTION OF PREFERRED EMBODIMENT

Referring to the drawings, the numeral 10 generally designates an ostomy appliance consisting essentially of an outer pouch 11 and an inner pouch 12. Both pouches are relatively flat (when empty) and are formed of thin, heat-sealable sheet materials. The inner pouch 12 is smaller than the outer pouch in which it is located and has a bodyside (rear) wall 12a and an obverse (front) wall 12b heat sealed together along their peripheral edges. The bodyside wall 12a of the inner pouch is provided with a stoma-receiving orifice 13 and an annular flange or wafer 14 is secured to the exterior surface of wall 12a about the orifice. The flange has an orifice 14a in register with orifice 13 and is formed of a pressure-sensitive adhesive material suitable for adhering to the peristomal skin surfaces of a patient. While the adhesive may be a medical-grade acrylic adhesive, it is most advantageously formed of a so-called skin barrier material that is soft, pliant, and has both wet and dry tack. Such skin barrier materials are well known in the ostomy field and are generally composed of an elastomeric adhesive such as polyisobutylene in which one or more hydrocolloids, such as carboxymethylcellulose, pectin, gelatin, guar gum or karaya, are dispersed. Reference may be had to U.S. Pat. Nos. 4,477,325 and 4,496,357 for a discussion of known skin barrier compositions and a disclosure of additional compositions having advantages which may also be utilized here. The bodyside surface of flange or ring 14 may be protected until use by a release sheet 15 (shown only in phantom in FIG. 3) formed of siliconized paper or other suitable material.

The outer pouch 11 similarly has a bodyside (rear) wall 11a and an obverse (front) wall 11b heat sealed together along their peripheral edges to define a chamber 16 in which the inner pouch is contained. Walls 11a and 11b are formed of thin, flexible heat-sealable film or sheet material that is water-insoluble and liquid, gas, and odor impermeable. The composition may be any of a variety of thermoplastic films used for conventional ostomy pouches. One material that has been found particularly effective is low density polyethylene coextruded with a coextensive layer or core of a polymer or copolymer of vinylidene chloride, known under the designation Saranex, from Dow Chemical Company, Midland, Mich., but other materials having similar properties may be used.

Since the outer pouch is formed of gas and odor impermeable material, conventional means are provided for venting the pouch and preventing it from inflating or ballooning in use. In the embodiment illustrated, such venting means takes the form of a small opening 17 formed in one of the walls, preferably bodyside wall 11a, well above stoma orifice 14a and adhesive flange 14. A deodorizing gas filter 18 of any suitable construction is secured to the inside (or outside) surface of the wall across vent opening 17 for deodorizing flatus escaping from the pouch. Reference may be had to U.S. Pat. Nos. 3,759,260, 4,203,445, and 4,274,848 for information on the construction and operation of flatus-deodorizing filters that may be used here.

Outer pouch 11 has an opening 19 in its bodyside wall 11a that is substantially larger than the stoma-receiving orifice 13 of the inner pouch 12. The opening is generally concentric with the orifice and surrounds the first adhesive flange ring 14. A second adhesive flange ring 20 is externally secured to the outer pouch about opening 19 and, as shown in the drawings, both the opening 19 of the pouch wall and the opening 20a of the annular flange 20 are substantially larger than the outer dimensions of the inner flange ring 14. The two flange rings are therefore spaced apart, resulting in a construction in which the inner and outer pouches are unconnected to each other in the area of the stoma-receiving orifice 13.

The term "concentric" is here used to mean that the outer flange ring 20 surrounds inner flange ring 14 with both rings having their centers in the same general area. While the rings are shown to be circular in outline in FIGS. 1 and 4, such circular configuration is not an essential requirement and, if desired, the concentric rings may assume other shapes such as, for example, oval shapes or square shapes with rounded corners. Furthermore, a combination of such shapes might be utilized. Thus, it may be desirable to provide outer flange ring 20 with an outer periphery that is generally square in outline, preferably with rounded corners, and an inner edge that is circular, in which case the inner flange ring 14 would have a correspondingly circular outer edge of smaller diameter than the opening 20a of the outer ring.

The composition of the outer flange ring 20 may be the same as or different than the composition of the inner flange ring 14. Both flange rings are formed of pressure-sensitive adhesive material, but the outer ring, being farther from the stoma and less likely to be exposed to stomal fluids, may be composed of any of a number of well known skinfriendly barrier materials that tend to be more susceptible to dissolution or disintegration when exposed to such fluids. Reference may be had to U.S. Pat. No. 5,496,296 for discussion of barrier materials in terms of softness, adhesive aggressiveness, skinfriendliness, fluid absorptiveness, and susceptibility to dissolution/disintegration upon exposure to stomal fluids.

Like inner adhesive flange ring 14, the outer flange ring 20 has its bodyside surface protected by an annular release sheet 21 formed of siliconized paper or other suitable material. In FIG. 3, such release sheets 15 and 21 are shown as separate concentric elements but, if desired, such sheets may be combined to provide a single temporary covering that protects the bodyside surfaces of the flange rings until the covering is stripped away at time of use. A unitary release sheet covering the adhesive surfaces of both flange rings would also serve the purpose of insuring that the rings are maintained in spaced condition during storage and handling of the appliance.

The obverse wall 11b of the outer pouch is provided with a pair of downwardly and outwardly diverging lines of weakness 22 that define a large generally triangular flap portion 23 having an end upper apex 23a near the upper limits of the pouch. Such lines of weakness may be straight or curvilinear and may take the form of narrow diverging bands or areas produced by contacting the thermoplastic material of the obverse wall with a thin-edged heating element during manufacture of the product. Alternatively, such lines may be in the form of perforations covered with strips of adhesive tape that are removed prior to opening of the outer pouch.

If desired, the lines of weakness may also have extensions 22a that are directed downwardly along the side edges of the outer pouch. Such extensions 22a may continue downwardly to points adjacent the lower end of the outer pouch or, as shown in FIG. 2, may terminate well above the pouch's lower end. In the latter case, it may be desirable to form the obverse wall 11b of a material that is directionally oriented so that it tears more readily in a vertical (machine) direction than in a horizontal (cross) direction. Tearing of the flap all the way to the bottom of the outer pouch might therefore be easily accomplished even though the extensions 22a are abbreviated in length. Alternatively, the divergent lines of weakness may extend to the heat-sealed peripheral side edges of the outer pouch so that the downward tearing of the flap may continue along the heat-sealed edges of that pouch.

To facilitate a tearing operation, gripping means may be provided at the apex 23a of the flap 23. In the illustration given, such gripping means takes the form of a flexible tab 24 having a lower portion 24a that is heat sealed or otherwise securely attached to the apex of the flap and an upper portion 24b that is unsecured to the pouch and may easily be gripped and pulled downwardly to initiate the tearing operation.

In the exploded view of FIG. 4, the bodyside and obverse walls 11a and 11b of the outer pouch are shown separated from inner pouch 12. It is to be noted that the inner pouch has its walls sealed together across the top of the pouch along a relatively wide upper marginal portion 25. The wide heat seal 25 is shown in FIG. 5 to consist of an upper section 25a and a lower section 25b. The upper section is in turn sealed, either thermally or adhesively, to at least one of the upper portions 26 or 27, and prefereably both of such portions, of the walls 11a and 11b of the outer pouch. The lower section 25b of the sealed marginal portion extends downwardly, preferably as shown without interruption of the seal, into the chamber 16 of the outer pouch—that is, the lower section 25b extends downwardly below the seal between upper section 25a and the walls of the outer pouch.

The lower section 25b of sealed marginal portion 25 is provided with means for defining a tear line extending across the full width, or substantially the full width, of the inner pouch. Such a tear line is shown in the drawings to be defined by a line of perforations 28 extending across the top of the inner pouch within the limits of the sealed lower section 25b but other techniques for producing a tear line, such as by thermally forming a line of indentation of reduced strength, may be used. If desired, the tear line may stop just short of the side edges of the inner pouch, or just short of the apex of the inner pouch, to provide limited areas of increased resistance to tearing, thereby reducing possibilities that the two pouches might become accidentally disconnected in use.

In the appliance as supplied to a user, the inner pouch is therefore secured in place within the outer pouch along the upper margins of the two pouches. When the appliance is oriented as shown in FIGS. 1–3, the inner pouch is effectively suspended within the chamber of the outer pouch by the combination of seals extending along the upper limits, which may include the upper sides, of both pouches. Since the inner pouch is both narrower and shorter than the outer pouch, a spacing exists within the chamber between the side and bottom edges of the inner pouch and those of the outer pouch (FIGS. 1–3). Such spacing tends to be stabilized in use where, as shown in the drawings, the seal that extends across the two pouches and joins them together is of substantial length.

The two-pouch appliance disclosed herein is particularly suitable for use in a system where the inner pouch is intended for disposal, along with its contents, into a flush toilet. For that purpose, the inner pouch may be formed of any material, or combination of materials, that allows the pouch to support liquid contents without dissolving or disintegrating and, because of its flexibility, thinness, and other properties, is suitable for discarding into a flush toilet connected to a municiple sewer system or septic system. For that purpose, the material of the inner pouch should be dissolvable or at least biodegradable. In most systems disclosed in the prior art, such flushability is achieved by forming the pouch from multilayer film materials, with the load-bearing properties of the inner pouch being provided by a water soluble polymer that is relatively strong and tough when dry but becomes limp, soft and/or slippery, and dissolves, disintegrates, or at least degrades, when externally exposed to the water in a toilet bowl. As disclosed in U.S. Pat. No. 4,372,311, such a polymer may be polyvinyl alcohol, poly(alkylene oxide), hydroxyethyl cellulose, hydroxypropyl cellulose, polyvinyl pyrrolidone, polyacrylamide, polyacrylic acid, or poly(vinyl methyl ether-co-maleic anhydride). The inner layer may be of any suitable material that is water insoluble and, at the same time, allows the inner surfaces of the walls to be sealed together, preferably by heat sealing, along the margins of the pouch. While various materials and combinations of materials have been disclosed in the art for achieving such purposes, one combination that is believed particular effective is disclosed in co-pending co-owned application Ser. No 363,936, filed Dec. 27, 1994, the disclosure of which is incorporated by reference herein. The multilayered film as disclosed in that application comprises a water-soluble/dispersible load bearing layer consisting essentially of a blend of polyethylene oxide and plasticized polyvinyl chloride laminated and bonded to a relatively thin and weak barrier layer of polyvinylidene chloride or a copolymer thereof.

Since the pouches are not connected together in the region of the stoma-receiving orifice when the appliance is in use, and since the outer pouch has a large flap along its obverse wall which may be easily torn downwardly to expose the inner pouch while the appliance is still attached to a patient, accessing the inner pouch, and separating and extracting it from the outer pouch, may be accomplished far more easily than with two-pouch appliances disclosed in the prior art. FIG. 6 schematically depicts appliance 10 adhesively secured to the abdomen of a wearer W after the user has pulled tab 24 downwardly to tear flap 23 away from the remainder of the obverse wall 11b of outer pouch 11. The inner pouch 12 containing waste material is exposed through the flap opening and, without significantly changing its orientation, a user may extract it from the outer pouch as indicated in FIG. 7. To do so, the adhesive flange ring 14 of the inner pouch is detached from the peristomal skin surfaces of the patient but such detachment is readily accomplished without disturbing the attachment between the flange ring 20 of the outer pouch 11 and the skin because the two rings are separate unconnected elements. Thereafter, the inner pouch is detached from the outer pouch by tearing the inner pouch free along its upper marginal tear line 28 (FIG. 8), and the inner pouch and its contents may then be discarded into a flush toilet. Thereafter, the outer pouch 11 may be peeled away along its adhesive attachment to the patient and discarded into any suitable waste receptacle.

While FIGS. 7 and 8 illustrate what appear as two separate steps, those steps may not necessarily be performed in the sequence shown. Thus, a wearer may prefer to tear the inner pouch free along its tear line 28 (FIG. 8) and thereafter extract the inner pouch from the outer pouch (FIG. 7). Moreover, it is believed apparent that both steps may be performed substantially simultaneously, the user drawing the inner pouch outwardly and downwardly at the same time that it is being detached along its tear line. Regardless of whether such steps are performed sequentially or simultaneously, the outer pouch may remain connected to the patient until the inner pouch and its contents have been removed and discarded. Furthermore, throughout all of such steps, the inner pouch retains essentially the same vertical orientation it assumed while it was worn by the patient, thereby reducing risks of spillage as such steps are being performed.

While in the foregoing, an embodiment of the invention has been disclosed in considerable detail for purposes of illustration, it will be understood by those skilled in the art that many of these details may be varied without departing from the spirit and scope of the invention.

We claim:

1. An ostomy appliance comprising an inner pouch having a bodyside wall and an obverse wall and having a stoma-receiving orifice in said bodyside wall; said inner pouch being located within a larger outer pouch; said outer pouch having a bodyside wall and an obverse wall with an opening in said bodyside wall generally concentric with and substantially larger than said orifice of said inner pouch; said inner pouch having a sealed upper marginal portion disposed between and sealed to an upper portion of at least one of said walls of said outer pouch; said sealed upper marginal portion of said inner pouch including a lower section located below the seal between said marginal portion and said outer pouch; said lower section of said marginal portion being provided with means defining a tear line extending across the upper end of said inner pouch; said bodyside wall of said inner pouch having a first annular adhesive flange externally secured thereto about said orifice; said bodyside wall of said outer pouch having secured to the bodyside wall thereof a second annular adhesive flange extending about and spaced from said first adhesive flange; said bodyside walls of said inner and outer pouches being unconnected to each other about said orifice; and means provided by said obverse wall of said outer pouch for accessing and extracting said inner pouch therefrom.

2. The appliance of claim 1 in which said upper marginal portion of said inner pouch is sealed to upper portions of one or both of said walls of said outer pouch.

3. The appliance of claim 1 in which said inner and outer pouches are each formed of thin, flexible, heat-sealable material; said seal between said marginal portion of said inner pouch and said upper wall portion of said outer pouch being a thermal or adhesive seal.

4. The appliance of claim 3 in which said bodyside and obverse walls of said inner pouch are heat sealed together to define said sealed upper marginal portion.

5. The appliance of claim 4 in which said means defining said tear line comprises a line of perforations along said lower section of said sealed marginal portion of said inner pouch.

6. The appliance of claims 3, 4 or 5 in which said means for accessing and extracting comprises a tearable flap portion provided by said obverse wall of said outer pouch.

7. The appliance of claim 6 in which said tearable flap portion is at least partially defined by downwardly and outwardly diverging lines of weakness in said obverse wall of said outer pouch.

8. The appliance of claim 7 in which said diverging lines of weakness consist of lines of reduced thickness in the material of said obverse wall of said outer pouch.

9. The appliance of claim 8 in which said lines of weakness define a generally triangular flap portion with an apex of said triangular flap portion located adjacent the upper limits of said upper marginal portion of said inner pouch.

10. The appliance of claim 9 in which means are provided at said apex for manually gripping and pulling said triangular portion to tear the same downwardly away from the remainder of said outer pouch.

11. A two-pouch ostomy appliance comprising an inner pouch having a bodyside wall and an obverse wall and having a stoma-receiving orifice in said bodyside wall; said inner pouch being suspended within a larger outer pouch; said outer pouch having a bodyside wall and an obverse wall with an opening in said bodyside wall generally concentric with and substantially larger than said orifice of said inner pouch; said inner pouch having a sealed upper marginal portion disposed between and sealed to an upper portion of at least one of said walls of said outer pouch; said sealed upper marginal portion of said inner pouch including a lower section located below the seal between said marginal portion and said walls of said outer pouch; said lower section of said marginal portion being provided with means defining a tear line extending across the upper end of said inner pouch.

12. The appliance of claim 11 in which said upper marginal portion of said inner pouch is sealed to upper portions of one or both of said walls of said outer pouch.

13. The appliance of claim 11 in which said inner and outer pouches are each formed of thin, flexible, heat-sealable material; said seal between said marginal portion of said inner pouch and said side walls of said outer pouch being a thermal or adhesive seal.

14. The appliance of claim 13 in which said bodyside and obverse walls of said inner pouch are sealed together to define said sealed upper marginal portion.

15. The appliance of claim 14 in which said means defining said tear line comprises a line of perforations along said lower section of said sealed marginal portion of said inner pouch.

16. The appliance of claim 11 in which means are provided by said obverse wall of said outer pouch for accessing and extracting said inner pouch therefrom.

17. The appliance of claim 16 in which said means for accessing and extracting comprises a tearable flap portion provided by said obverse wall of said outer pouch.

18. The appliance of claim 17 in which said tearable flap portion is at least partially defined by downwardly and outwardly diverging lines of weakness in said obverse wall of said pouch.

19. The appliance of claim 18 in which said lines of weakness define a generally triangular flap portion having an apex located adjacent the upper limits of said marginal portion of said inner pouch.

20. The appliance of claim 19 in which means are provided at said apex for manually gripping and pulling said triangular portion to tear the same downwardly away from the remainder of said outer pouch.

* * * * *